US009339421B2

(12) United States Patent  (10) Patent No.: US 9,339,421 B2
Glahn et al.  (45) Date of Patent: May 17, 2016

(54) ABSORBENT ARTICLE HAVING MULTIPLE GRAPHIC ZONES

(71) Applicant: The Procter & Gamble Company, Cincinnati, OH (US)

(72) Inventors: Tina Marie Glahn, Cincinnati, OH (US); Rachael Eden Walther, Union, KY (US); Gary Dean Lavon, Liberty Township, OH (US); Amanda Margaret Bicking, Cincinnati, OH (US); Diana Woehnl Juratovac, Columbus, OH (US); Sara Jon Shipley, Columbus, OH (US); Vanessa Melendez, Cincinnati, OH (US); Fred Naval Desai, Fairfield, OH (US); Margaret Henderson Hasse, Wyoming, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 116 days.

(21) Appl. No.: 13/893,643

(22) Filed: May 14, 2013

(65) Prior Publication Data

US 2013/0310798 A1 Nov. 21, 2013

Related U.S. Application Data

(60) Provisional application No. 61/646,953, filed on May 15, 2012.

(51) Int. Cl.
*A61F 13/15* (2006.01)
*A61F 13/51* (2006.01)
*A61F 13/514* (2006.01)
*A61F 13/84* (2006.01)

(52) U.S. Cl.
CPC ........... *A61F 13/51* (2013.01); *A61F 13/51496* (2013.01); *A61F 2013/8497* (2013.01)

(58) Field of Classification Search
CPC .................. A61F 2013/8497; A61F 13/51496
USPC ................................ 604/385.01, 385.02, 392
See application file for complete search history.

(56) References Cited

U.S. PATENT DOCUMENTS 6,352,528 B1 * 3/2002 Weber et al. ............. 604/385.03
6,590,136 B1  7/2003 Young et al.

(Continued)

FOREIGN PATENT DOCUMENTS

JP 2003-070838 A 3/2003
JP 2005-296372 A 10/2005

*Primary Examiner* — Jacqueline Stephens
(74) *Attorney, Agent, or Firm* — Andrew J. Mueller

(57) ABSTRACT

An absorbent article includes a first waist region, a second waist region, and a crotch region, wherein the first waist region and second waist region are joined with each other such that a pair of side seams are formed and the absorbent article has two leg openings and a waist opening. At least one of the first waist region or the second waist region include a first graphic zone, a second graphic zone, and a third graphic zone, wherein the first graphic zone, the second graphic zone, and the third graphic zone are disposed at a side seam of the absorbent article.

14 Claims, 11 Drawing Sheets

(56) References Cited

U.S. PATENT DOCUMENTS

| | | |
|---|---|---|
| 6,664,439 B1 | 12/2003 | Arndt et al. |
| 6,989,006 B2 | 1/2006 | Lavon et al. |
| 7,695,463 B2 | 4/2010 | Lavon et al. |
| 7,896,858 B2 | 3/2011 | Trennepohl et al. |
| 7,931,636 B2 | 4/2011 | Lavon et al. |
| 2001/0031954 A1* | 10/2001 | Jordan et al. ............. 604/385.01 |
| 2003/0158532 A1* | 8/2003 | Magee et al. ............ 604/385.01 |
| 2005/0143698 A1* | 6/2005 | Sosalla et al. ................. 604/367 |
| 2007/0142798 A1 | 6/2007 | Goodlander et al. |
| 2009/0247979 A1* | 10/2009 | Sosalla et al. ............ 604/385.01 |

* cited by examiner

ABSORBENT ARTICLE HAVING MULTIPLE GRAPHIC ZONES

FIELD OF THE INVENTION

The present invention relates to absorbent articles having multiple graphic zones.

BACKGROUND OF THE INVENTION

Infants and other incontinent individuals children and adults) wear disposable absorbent articles such as diapers and adult incontinence products to receive and contain urine and other body exudates. Training pants or pull-on diapers have become popular for use on children able to walk and often who are toilet training, and adult incontinence products have become increasingly common for use on adults to assist with incontinence issues. Many disposable pull-on garments use elastic elements secured in an elastically contractible condition in the waist and/or leg openings. Typically, in order to insure full elastic fit about the leg and the waist such as is provided with durable undergarments, the leg openings and waist opening are encircled at least in part with elasticized bands of rubber or other materials positioned along the periphery of the respective opening.

Disposable absorbent articles having an absorbent main body to cover the crotch region of the wearer and a belt defining the waist opening and leg openings are known in the art. However, current executions of a belted absorbent article only comprise graphics on the main body of the article and not on the belt. Having coordinated and integrated graphics on both the main body and the belt of an absorbent article can improve application and removal of the article, as well as provide more of an underwear-like look and feel, aiding in toilet training. Moreover, the more of an underwear-like look and feel that an absorbent article possesses, the more likely that a user will be willing to accept utilizing the product.

Based on the foregoing, there is a need for a disposable absorbent article to provide an improved application and removal of the article. There is also a need for a disposable absorbent article to provide an underwear-like look and feel.

SUMMARY OF THE INVENTION

An absorbent article having a first waist region, a second waist region, and a crotch region. The first waist region and second waist region are joined with each other such that a pair of side seams or closures are formed such that the absorbent article has two leg openings and a waist opening. At least one of the first waist region and the second waist region may have a first graphic zone, a second graphic zone, and a third graphic zone. The first graphic zone, the second graphic zone, and the third graphic zone may be disposed at a side seam of the absorbent article. The crotch region may have a crotch region graphic zone such that the second graphic zone and the crotch region graphic zone are aligned to create a uniform graphical element. At least one of the first waist region or the second waist region may have a first graphic zone disposed adjacent the waist edge, and a third graphic zone disposed at or adjacent the leg opening.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which like designations are used to designate substantially identical elements, and in which:

DETAILED DESCRIPTION OF THE INVENTION

As used herein, the term "pull-on garment" refers to articles of wear which have a defined waist opening and a pair of leg openings and which are pulled onto the body of the wearer by inserting the legs into the leg openings and pulling the article up over the waist. The term "disposable" is used herein to describe garments which are not intended to be laundered or otherwise restored or reused as a garment (i.e., they are intended to be discarded after a single use and, preferably, to be recycled, composted or otherwise disposed of in an environmentally compatible manner). The pull-on garment is also preferably "absorbent" to absorb and contain the various exudates discharged from the body. A preferred embodiment of the absorbent article is the disposable absorbent pull-on garment, shown in FIG. 1.

As used herein, the term "absorbent article" refers to pull-on garments generally worn by infants and other incontinent individuals to absorb and contain urine, feces and/or menses. It should be understood, however, that the term absorbent article is also applicable to other garments such as training pants, incontinent briefs, feminine hygiene garments, and the like.

As used herein, the terms "elastic," "elastomer," and "elastomeric" refer to a material, which generally, is able to extend to a strain of at least 50% without breaking or rupturing, and is able to recover substantially to its original dimensions after the deforming force has been removed.

As used herein, the term "graphic" refers to a visual presentation and encompasses visual presentations formed from printing, aperturing, texturing, bonding, embossing, cutouts, etc.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

Figure 1:
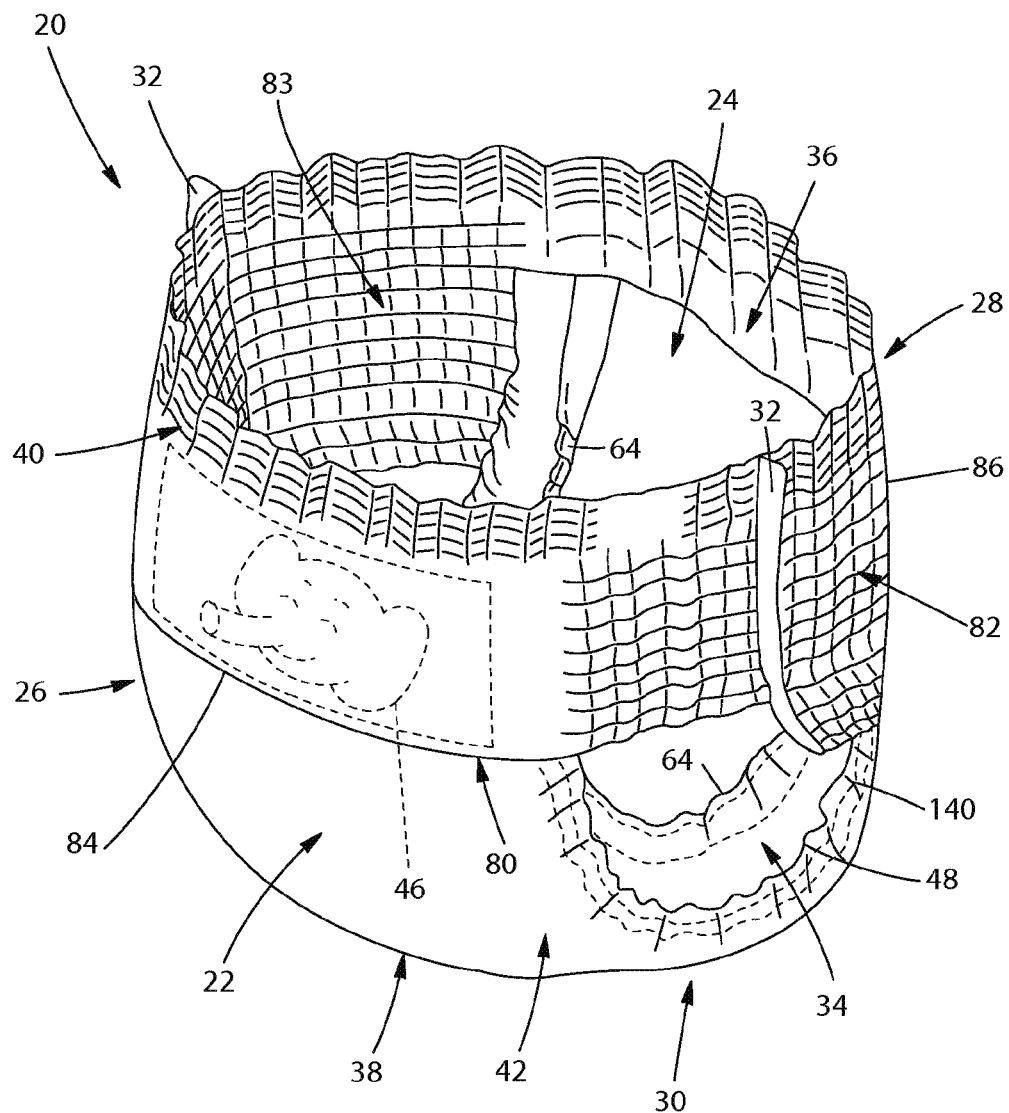
FIG. 1 is a perspective view of an exemplary disposable pull-on garment in a typical in-use configuration.
Figure 2:
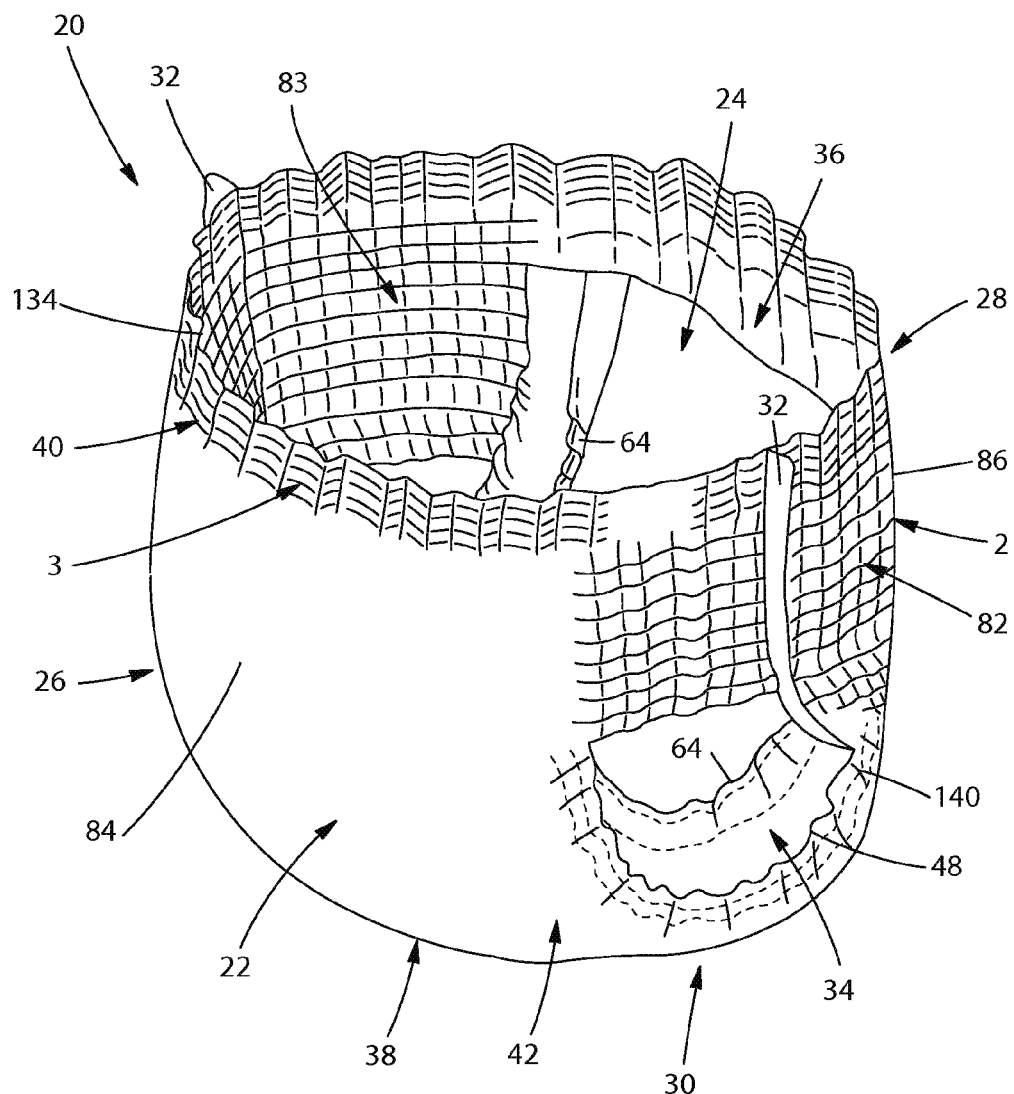
FIG. 2 is a perspective view of an exemplary disposable pull-on garment in a typical in-use configuration.

FIG. 1 is a perspective view of the absorbent article 20. FIG. 2 is a perspective view of the absorbent article 20. The absorbent article 20 has a longitudinal centerline L1 and a transverse centerline T1 (refer to FIG. 3 as well). The absorbent article 20 has an outer surface 22, an inner surface 24 opposed to the outer surface 22, a first waist region 26, a second waist region 28, a crotch region 30, and seams 32 which join the first waist region 26 and the second waist region 28 to form two leg openings 34 and a waist opening 36.

Figure 3:
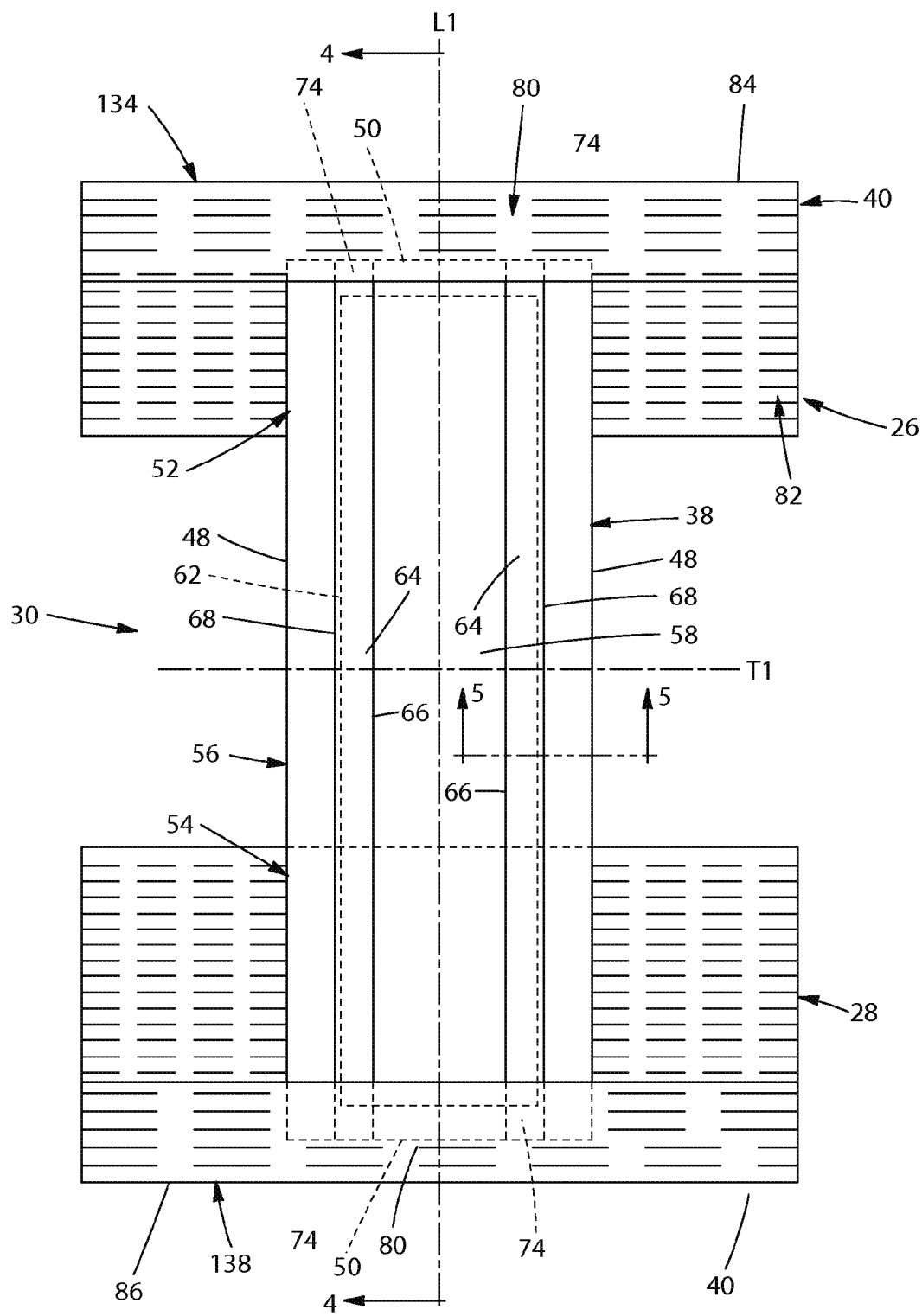
FIG. 3 is a plan view of the pull-on garment in its flat uncontracted condition showing the inner surface.

In the embodiment shown in FIGS. 1 and 3, the absorbent article 20 comprises an absorbent main body 38 (hereinafter may be referred to as "main body") to cover the crotch region of the wearer and a belt 40 extending transversely about the waist opening 36. The absorbent article 20 may also comprise an outer cover layer 42 to cover the main body 38. The belt 40 may define part, or all, of the waist opening 36. One or more of the belt 40, the main body 38 and/or the outer cover layer 42 may define portions of the leg opening 34. The absorbent article 20 may have an indicia 46 printed thereon, which may be disposed in the first waist region 26 and/or the second waist region 28.

In the embodiment shown in FIG. 2 the absorbent article 20 comprises an absorbent main body 38 to cover the crotch region of the wearer and a belt 40 extending transversely about the waist opening 36. The absorbent article 20 may also comprise an outer cover layer 42 to cover the main body 38. The belt 40 defines the waist opening 36. The belt 40, the main body 38 and/or the outer cover layer 42 may jointly define the leg opening 34. One or more of the belt layers may extend from a first waist edge 134 in a first waist region 26 through the crotch region to a longitudinally opposing second waist edge 138 in a second waist region 28 and forming a portion of the outer surface of the absorbent article 20.

The absorbent main body 38 absorbs and contains body exudates disposed on the main body 38. In the embodiment shown in FIG. 3, the main body 38 may have a generally rectangular shape having a longitudinal centerline L1, a transverse centerline T1, left and right longitudinally extending side edges 48 (hereinafter may be referred to as "longitudinal side edge") and first and second transversely extending end edges 50 (hereinafter may be referred to as "transverse end edge"). The main body 38 also has waist panels (i.e., a first waist panel 52 positioned in the first waist region 26 of the absorbent article 20 and a second waist panel 54 positioned in the second waist region 28) and a crotch panel 56 in the crotch region 30 between the first and second waist panels 52, 54.

Figure 4A:
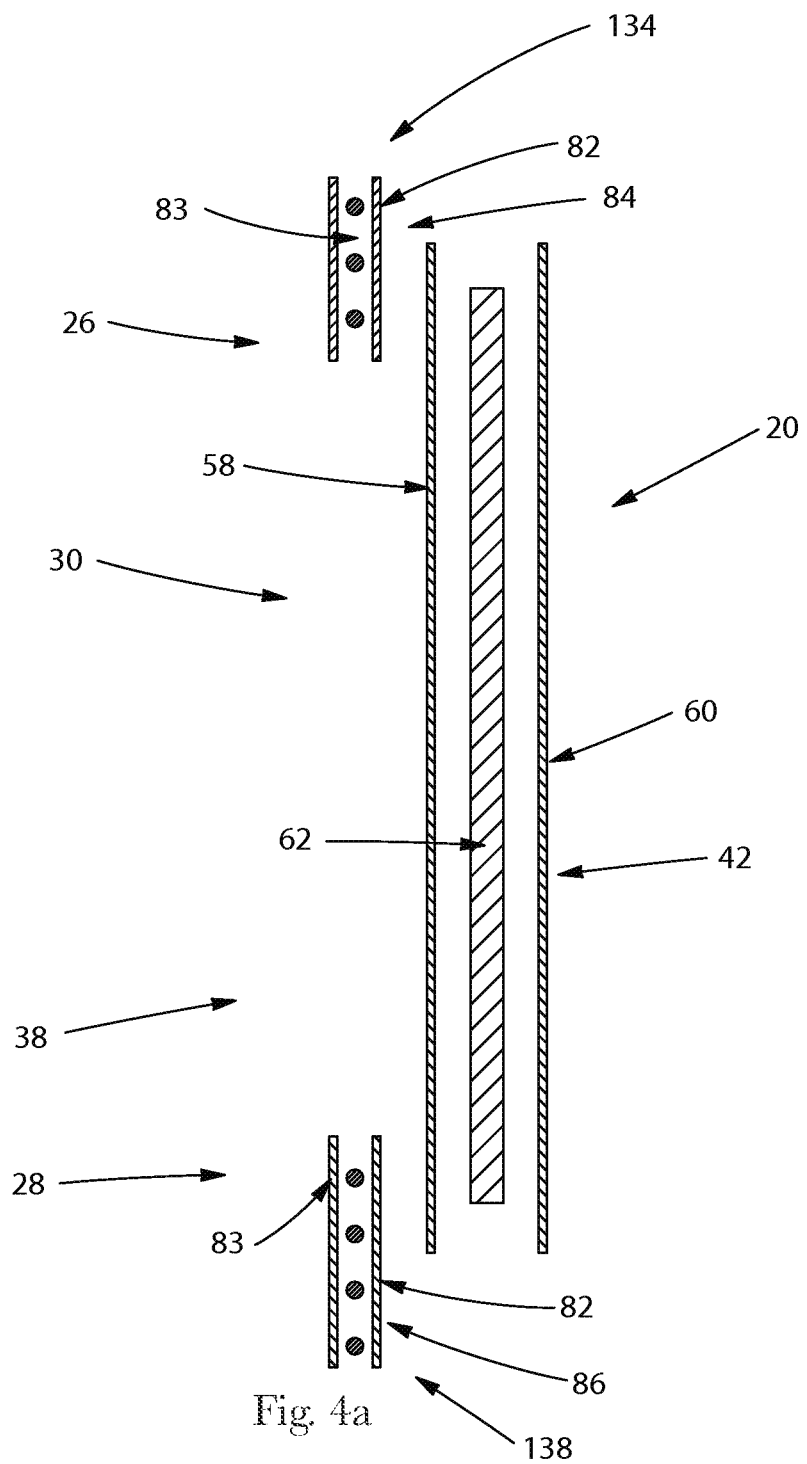
FIG. 4*a* is a schematic cross section view of a first embodiment taken along line 4-4 in FIG. 3 of an exemplary disposable pull-on garment.
Figure 4B:
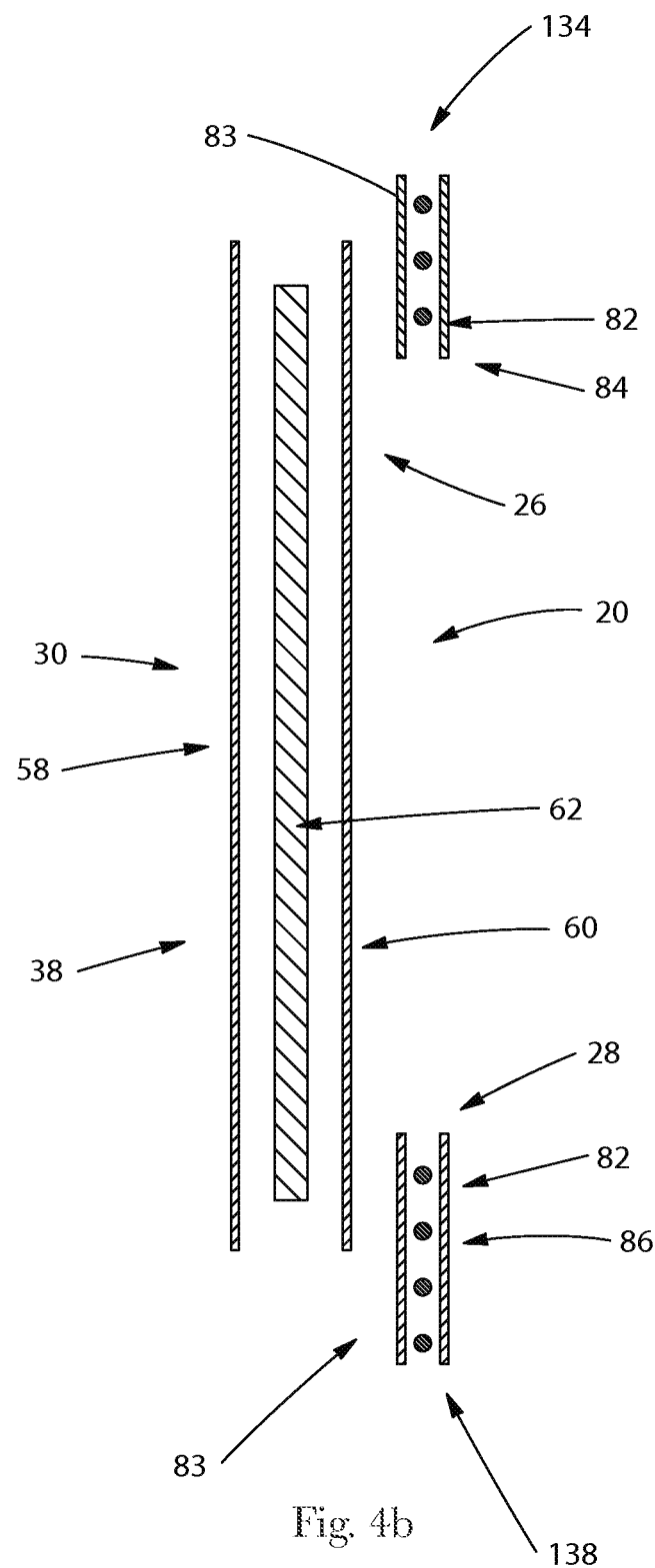
FIG. 4*b* is a schematic cross section view of a second embodiment taken along line 4-4 in FIG. 3 of an exemplary disposable pull-on garment.

In the embodiment shown in FIGS. 4a and 4b, the absorbent articles 20 may comprise first and second belts 84, 86 intended to encircle at least a portion of the waist of the wearer, the first and second belt portions 84, 86 being connected by a main body 38 forming the crotch region 30 of the absorbent article 20. The first and second belts 84 and 86 may be formed from a first belt layer forming a portion of the outer surface 22 of the absorbent article, the first belt layer 82 may be formed of two longitudinally spaced webs of material. The first and second belts 84 and 86 may also comprise a second belt layer 83 forming a portion of the inner surface 24 of the absorbent article 20, the second belt layer 83 may also be formed of two longitudinally spaced webs of material. The second belt layer may also be discontinuous and spaced apart in a transverse direction. The first and second belt layers 82, 83 may be formed of substantially the same material or may comprise different materials. The first and second belt layers 82, 83 may be formed from nonwovens, films, foams, elastic nonwoven, or combinations thereof. The first and second belts 84, 86 may also comprise an elastomeric material disposed between the first and second belt layers 82, 83. The elastomeric material may comprise one or more elastic strands, elastomeric films, elastomeric ribbons, elastomeric nonwovens, elastomeric filaments, elastomeric adhesives, elastomeric foams, scrims or combinations thereof. In certain embodiments, one or both of the first and second belt layers 82 and 83 may be formed from an elastomeric material as described above. A portion of the elastomeric material may be directly combined with the outer cover layer. The main body 38 of the absorbent article may comprise an outer surface 22, backsheet 60, an inner surface 24, topsheet 58, and an absorbent core 62 disposed between the topsheet 58 and the backsheet 60. The backsheet may be formed of a nonwoven material, woven material, films or laminates comprising a combination of one or more of these materials. In one embodiment the backsheet is a film and nonwoven laminate wherein the nonwoven of the laminate is the outer cover layer. In addition, the main body 38 may comprise elasticized barrier leg cuffs 64 disposed at or adjacent the side edges of the main body. The first and second belts 84, 86 may overlap at least a portion of the main body and one or both of the belt portions may be disposed on the outer surface of the main body or alternatively on the inner surface of the main body. A portion of the second belt layer and/or a portion of the first belt layer may be directly attached to or formed by the outer cover layer. Alternatively, the first belt and second belt 84, 86 may comprise longitudinally spaced webs of material forming a first surface of the belt wherein the webs are folded along the waist edge, or alternatively the leg opening edge, of the belt to wrap the elastomeric material and form at least a portion of the second surface of the belt. In other words, at least a portion of the inner surface and outer surface of each of the belt portions may be formed from a single web of material.

Figure 5:
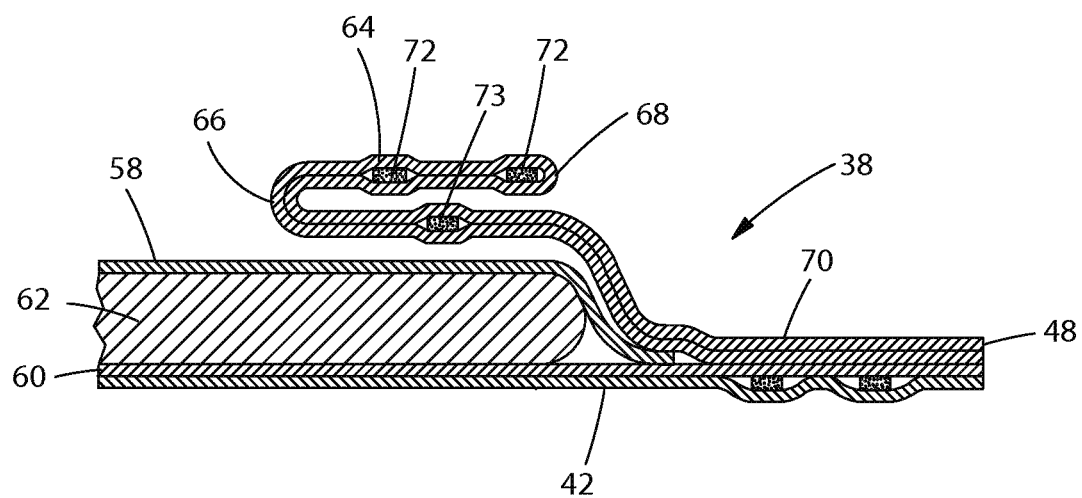
FIG. 5 is a schematic cross section view taken along line 5-5 in FIG. 3 of an example of a folded outer leg cuff suitable in one embodiment of the invention.

The main body 38 may comprise a liquid pervious topsheet 58, a liquid impervious backsheet 60 and an absorbent core 62 disposed therebetween. The main body 38 may additionally comprise a barrier leg cuff 64 disposed along the longitudinal side edge 48. The barrier leg cuff 64 provides improved containment of liquids and other body exudates in the crotch region 30. The barrier leg cuff 64 shown in FIG. 5 comprises a single layer of material which may be folded to form a barrier leg cuff having two layers. The barrier leg cuff 64 extends from the side of the main body at or adjacent the longitudinal side edge 48 toward the longitudinal centerline L1. The barrier leg cuff may be folded along the folding line 66 back toward the longitudinal side edge 48. The barrier leg cuff 64 may have a first barrier cuff elastic material 72 adjacent to the proximal portion 68 and a second barrier cuff elastic material 73 adjacent to the distal portion 70 of the barrier leg cuff 64. The distal portion 70 of the barrier leg cuff 64 may be joined to the backsheet 60 adjacent to the longitudinal side edge 48. The portion of the barrier leg cuff 64 along the folding line 66 and the proximal portion 68 may be free from attachment to any portion of the main body 38 in the crotch region 30 such that the barrier leg cuff 64 stands up toward the wearer's body. The longitudinal ends 74 of the barrier leg cuff 64 may be joined to the topsheet 58 at or adjacent the longitudinally opposing ends of the leg cuff by an attachment means which may be any known means such as an adhesive, heat bond, pressure bond or the like as shown in 5.

Other barrier leg cuff embodiments also useful in the present invention are disclosed in U.S. Pat. Nos. 7,931,636 and 7,695,463.

The liquid pervious topsheet 58 may be positioned adjacent the body-facing surface of the absorbent core 62 and may be joined thereto and/or to the backsheet 60 by any attachment means known in the art. The liquid impervious backsheet 60 is generally that portion of the absorbent article 20 positioned adjacent the garment-facing surface of the absorbent core 62 and prevents the exudates absorbed and contained therein from soiling articles that may contact the absorbent article 20. The absorbent core is positioned between the topsheet 58 and the backsheet 60 and absorbs and retains liquids such as urine and other certain body exudates.

The topsheet 58, the backsheet 60 and the absorbent core may be manufactured from many known materials. Suitable topsheet materials may include porous foams; reticulated foams; apertured plastic films; or woven or nonwoven webs of natural fibers (e.g., wood or cotton fibers), synthetic fibers e.g., polyester or polypropylene fibers), or a combination of natural and synthetic fibers. Suitable backsheet materials may include breathable materials that permit vapors to escape from the diaper while still preventing exudates from passing through the backsheet and may be formed from films, microporous and/or monolithic films, woven and nonwoven webs and the like as well as combinations of these materials. The woven or nonwoven webs of the backsheet may be formed of natural fibers (e.g., wood or cotton fibers), synthetic fibers (e.g., polyester or polypropylene fibers), or a combination of natural and synthetic fibers.

A suitable absorbent core for use in the absorbent article 20 may comprise any absorbent material which is generally compressible, conformable, non-irritating to the wearer's skin, and capable of absorbing and retaining liquids such as urine and other certain body exudates. In addition, the configuration and construction of the absorbent core may also be varied (e.g., the absorbent core(s) or other absorbent structure(s) may have varying caliper zones, hydrophilic gradient(s), a superabsorbent gradient(s), or lower average density and lower average basis weight acquisition zones; or may comprise one or more layers or structures). In some embodiments, the absorbent core may comprise one or more elements including a fluid acquisition component, a fluid distribution component, and a fluid storage component. Examples of a suitable absorbent core having a fluid acquisition component, a fluid distribution component, and a fluid storage component are described in U.S. Pat. Nos. 6,590,136, 6,664,439 and 6,989,006.

The outer cover layer 42 may be disposed on the outer surface 22 of the absorbent article 20 to cover at least the crotch panel 56 of the absorbent main body 38. The outer cover layer 42 may extend into and cover the first waist panel 52 and the second waist panel 54 of the main body 38. The outer cover layer may form a portion of the backsheet and/or the main body. The outer cover layer 42 may be directly joined to and cover a portion or all of the liquid impervious backsheet 60 of the main body 38. The central panel 80 of the first and second belt 84, 86 may be joined to the first waist panel 52 and the second waist panel 54 of the main body 38 through the outer cover layer 42. Thus, the outer cover layer 42 is disposed between the first and second belt 84, 86 and the liquid impervious backsheet 60 of the main body 38. In one embodiment shown in FIG. 2, the outer cover layer 42 is coextensive with the liquid impervious backsheet 60. The leg elastic material 140 may be disposed so as to extend generally longitudinally along the longitudinal side edge 48 of the main body 38. The leg elastic material 140 may be disposed at least in the crotch region 30 of the absorbent article 20 or may be disposed along the entirety of the longitudinal side edge 48.

The outer cover layer 42 may comprise a material separate from the material of the inner layer 83 and/or the outer layer 82 constituting the belt 40. The outer cover layer 42 may comprise two or more layers of materials. The outer cover layer 42 may comprise any known materials and may comprise materials used for the first and second belt 84, 86 as explained above. The outer cover layer 42 may comprise a single layer of nonwoven web of synthetic fibers, natural fibers or combinations of natural and synthetic fibers. The outer cover layer 42 may comprise a single layer of hydrophobic, non-stretchable nonwoven material. The outer cover layer may comprise a film, a foam, a nonwoven, a woven material or the like and/or combinations thereof such as a laminate of a film and a nonwoven.

The belt 40 comprises a first belt 84 and a second belt 86 (hereinafter may be referred to as front and back belt 84, 86) and has a ring-like configuration by permanently or rethstenably connecting the first belt 84 and the second belt 86 at the seams 32. The belt 40 may be ring-like and elastic. The ring-like elastic belt 40 extends transversely about the waist opening 36 of the absorbent article 20 and acts to dynamically create fitment forces and to distribute the forces dynamically generated during wear.

The first and second belt 84, 86 may comprise any known materials. Suitable material for the first and second belt 84, 86 can be manufactured from a wide range of materials such as plastic films; apertured plastic films; woven or nonwoven webs of natural materials (e.g., wood or cotton fibers), synthetic fibers (e.g., polyolefins, polyamides, polyester, polyethylene, or polypropylene fibers), or a combination of natural and/or synthetic fibers; or coated woven or nonwoven webs. The belt may comprise a nonwoven web of synthetic fibers. The belt may comprise a stretchable or elastomeric nonwoven, elastomeric film, strands, ribbons or the like and combinations thereof. The belt may comprise an inner hydrophobic, non-stretchable nonwoven material and an outer hydrophobic, non-stretchable nonwoven material.

Pull-on garments may be made by providing distinct first 26 and second waist regions 28 from the crotch region 30, wherein the first 26 and second waist region 28 are formed in part by first and second elastomeric belts 84, 86. A main body 38 comprising an absorbent core in the crotch region 30 is attached to the inner, wearer-facing side of the first 84 and second elastomeric belts 86 at each longitudinal end of the main body 38.

The present invention is directed to a pull-on garment that provides ease of application and removal through the use of graphics. Further, the present invention is directed to a pull-on garment having an underwear-like look and feel through the use of graphics, aiding in user acceptance and toilet training. In currently available pull-on garments, graphics are typically printed only on the main body of the article. The outer layer of the main body at regions overlapping with the elastomeric belts, visible from outside the article, are typically utilized for providing graphics. Thus, the present invention is directed to multiple zones of graphics disposed on a multi-piece absorbent article comprising a main body and elastomeric belts in order to aid in product application and removal and to aid in size appropriateness of the article as well as assist in the toilet training of the wearer. The present invention is also directed to multiple zones of graphics disposed on a multi-piece absorbent article comprising a main body and elastomeric belts in order to provide an absorbent article with a more underwear-like look and feel, leading to greater acceptance by the wearer.

The graphics detailed herein may be provided by any method known in the art which will provide a visual presentation. As non-limiting examples, the graphics may be printed in the graphic zones, created through aperturing, texturing, cutting, embossing and/or bonding a material that is present in the graphic zones, or combinations thereof. Exemplary types and methods of aperturing and/or texturing zones of absorbent articles are disclosed in Ser. Nos. 13/893,405, 13/893,735, 13/893,634 and 13/893,658 all of which are being filed concurrently with this application. Printing one or more zone of an absorbent article, with or without additional texturing, aperturing, cutting, bonding and/or embossing in one or more zone of the absorbent article, provides the absorbent article with more underwear-like appearance. Likewise, texturing, aperturing, cutting, bonding and/or embossing one or more zone of an absorbent article, with or without additional printing in one or more zone of the absorbent article, provides the absorbent article with more underwear-like feel and appearance (e.g., softer, more cloth-like, lacey, etc.).

For pull-on absorbent articles intended for children in and beyond the toilet training period, an underwear like appearance, as opposed to an overall white diaper-like appearance, may have a significant psychological influence on the child and therefore be important to full engagement of the child in the training experience. Likewise, for pull-on absorbent articles intended for adults experiencing incontinence, an underwear like appearance, as opposed to an overall white diaper-like appearance, may have a significant psychological influence on the adult and therefore be important in gaining the adult's acceptance in using the absorbent articles. Broad areas of creating graphics on both the main body and elastomeric belts extending from the first waist region, crotch region, and second waist region, is one effective way of providing an underwear-like appearance.

Further, graphics herein may also include indicia (e.g., printing, aperturing, texturing, etc.) for indicating the front and/or back of the article. Indicia may also include one or more indication of size, gender, pulling area, etc. Pull-on absorbent articles may have different configurations for the front and back of the article, including but not limited to, greater area of material in the back side for covering the buttocks, uneven distribution of absorbent material in the crotch region for effectively absorbing and containing bodily fluids, etc. Unlike taped absorbent articles which may define the front and back of the article by the configuration of the tape and tape landing zone, the front and back distinction of a pull-on absorbent article may not be obvious to the wearer or caregiver just by the structure of the article. As such, the front and/or back of the article may be clearly communicated on both the main body, the elastomeric belts and combinations thereof to provide the expected performance of the article.

The combinations of the various graphic zones described herein, may be coordinated to create a uniform graphical element, such as common colors, associated shapes, common textures or patterns of texturing and/or aperturing, etc.

The first graphic zone 102 refers to the area of graphics disposed on one or more of the materials forming the elastomeric belt 84, 86 disposed at or near the first and/or second waist edge 134, 138 of the absorbent article 20. In some embodiments, the first graphic zone 102 may be continuous about the waist circumference of the absorborbent article.

The second graphic zone 104 refers to the area of graphics disposed on one or more of the materials forming the elastomeric belt 84, 86 disposed at or near the leg openings 34 of the absorbent article 20. In some embodiments, the second graphic zone 104 may extend from the side seam 32 of the absorbent article to the edge of the crotch region 30. The second graphic zone 104 can be continuous and form a portion of the main body graphics zone 108. The second graphic zone 104 can also be contiguous with at least a portion of the main body graphic zone 108 or the crotch graphic zone 110 (making a composite graphic zone). Accordingly, this composite graphic zone can extend from the side seam in one waist region through the crotch and to the side seam in the opposing waist region.

The third graphic zone 106 refers to the area of graphics disposed on one or more of the materials forming the elastomeric belt 84, 86 disposed between the first graphic zone 102 and the second graphic zone 104. In some embodiments, the third graphic zone 106 may be continuous from a one side seam to the opposing side seam, and continuous from a first waist region to a second waist region. The third graphic zone 106 can also form a composite graphic zone with the main body graphic 108 and/or the crotch graphic 110.

The main body graphic zone 108 refers to the area of graphics disposed on the main body 38 of the absorbent article 20. A portion of the main body graphic zone 108 may be disposed under portions of the first elastomeric belt 84 and/or second elastomeric belt 86. The main body graphic zone 108 may be present in the same areas as the first graphic zone 102, second graphic zone 104, or third graphic zone 106 for example, when the main body graphic zone is disposed on an outer cover layer that extends from a first waist end edge to a longitudinally opposing second waist end edge.

The crotch region graphic zone 110 refers to the area of graphics disposed on the main body 38 of the absorbent article 20 in the crotch region 30 of the absorbent article 20. The crotch region graphic zone 110 is disposed between the elastomeric belts 84, 86 and is not underlying the belts.

Figure 6A:
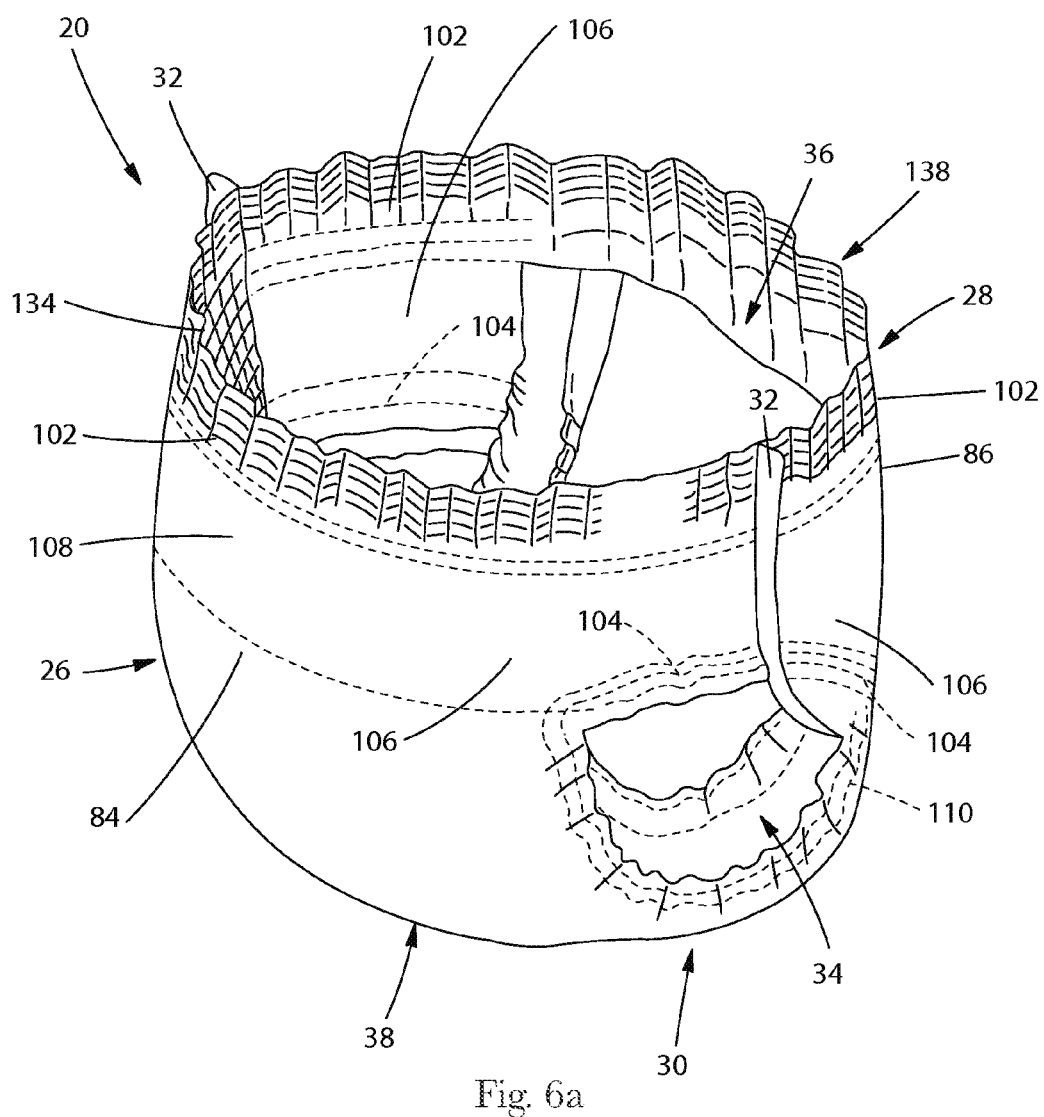
FIG. 6*a* is a perspective view of an exemplary disposable pull-on garment in a typical in-use configuration.

In the embodiment shown in FIG. 6a, the absorbent article 20 may comprise a first graphic zone 102, a second graphic zone 104, a third graphic zone 106, and a crotch region graphic zone 110. In this embodiment, the first graphic zone 102, the second graphic zone 104, and the third graphic zone 106 are present at a side seam 32 of the absorbent article 20. The first graphic zone 102 is disposed at or adjacent a waist edge 134, 138 and extends circumferentially about the first waist region 26 and/or the second waist region 28 of the absorbent article 20. The second graphic zone 104 is disposed at or adjacent a leg opening 34 and extends circumferentially about at least a portion of the leg opening 34. The third graphic zone 106 is disposed between the first graphic zone 102 and the second graphic zone 104 and extends circumferentially about at least a portion of the first waist region 26 and/or the second waist region 28 of the absorbent article 20. Thus, in this embodiment, a longitudinal axis of the absorbent article 20 extends through the first graphic zone 102 and the third graphic zone 106 but not the second graphic zone 104.

Further, as shown in FIG. 6a, the crotch region 30 may comprise a crotch region graphic zone 110 such that the second graphic zone 104 and the crotch region graphic zone 110 are aligned to create a composite graphical element that may or may not be uniform. Thus, the transition between the second graphic zone 104 and the crotch region graphic zone 110 may extend from the side seam 32 to an area at or adjacent the leg opening 34 in the crotch region forming a uniform graphical element around the leg opening 34.

Figure 6B:
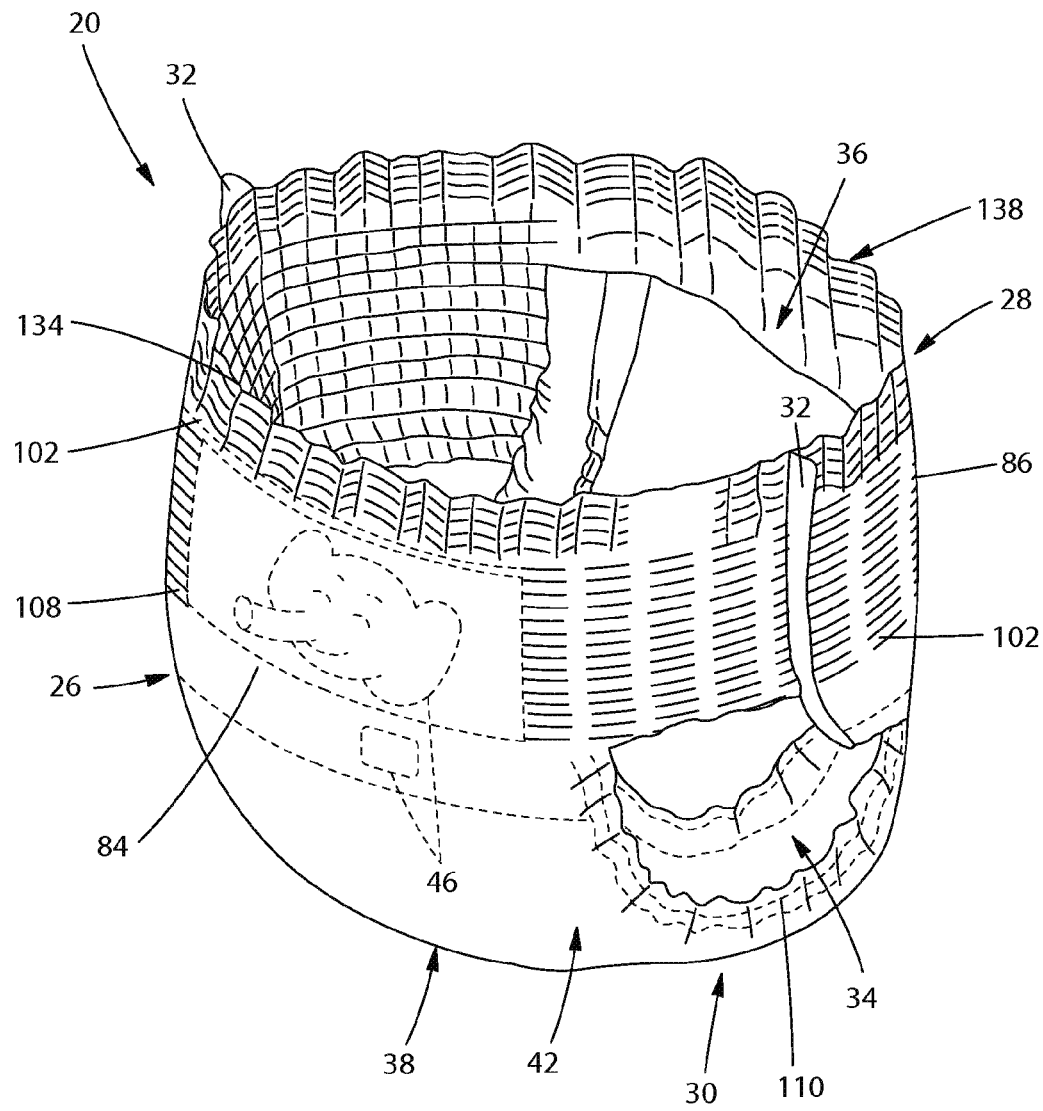
FIG. 6*b* is a perspective view of an exemplary disposable pull-on garment in a typical in-use configuration.
Figure 7A:
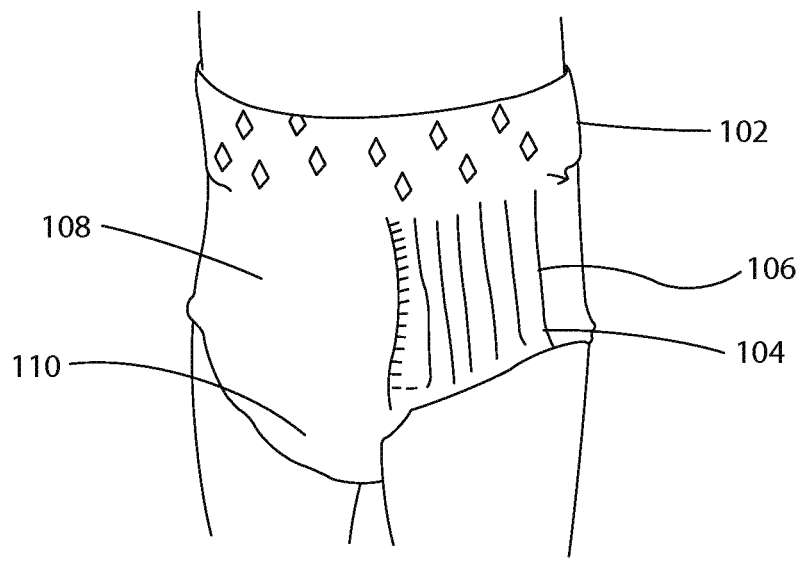
FIG. 7*a* is a perspective view of an exemplary disposable garment in a typical in-use configuration.
Figure 7B:
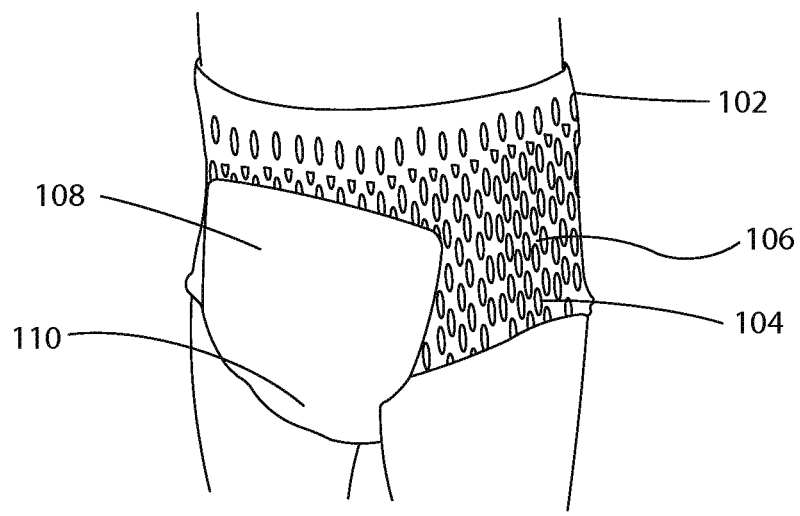
FIG. 7*b* is a perspective view of an exemplary disposable pull-on garment in a typical in-use configuration.
Figure 7C:
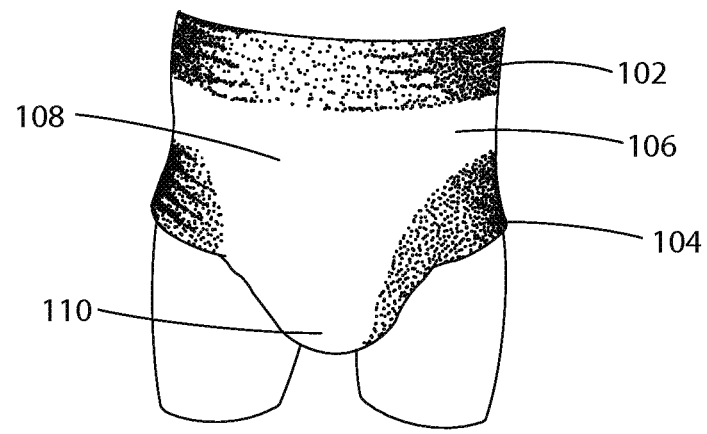
FIG. 7*c* is a perspective view of an exemplary disposable pull-on garment in a typical in-use configuration.
Figure 7D:
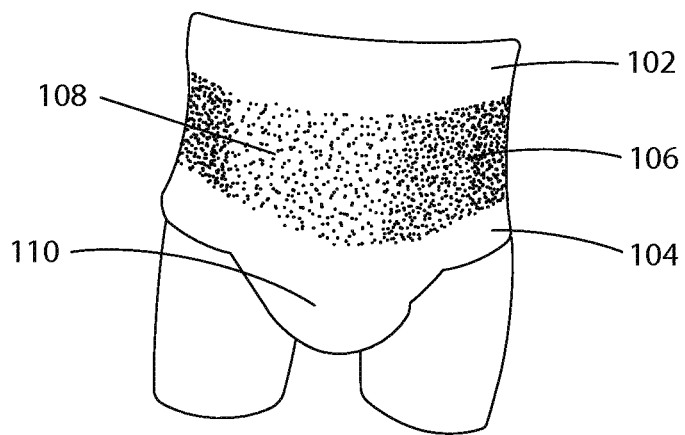
FIG. 7*d* is a perspective view of an exemplary disposable pull-on garment in a typical in-use configuration.
Figure 7E:
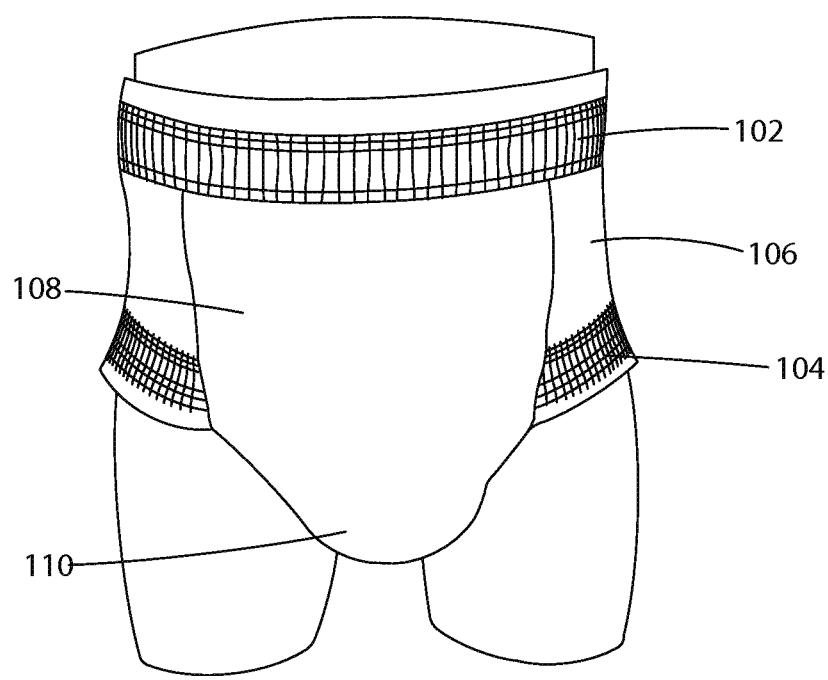
FIG. 7*e* is a perspective view of an exemplary disposable pull-on garment in a typical in-use configuration.
Figure 7F:
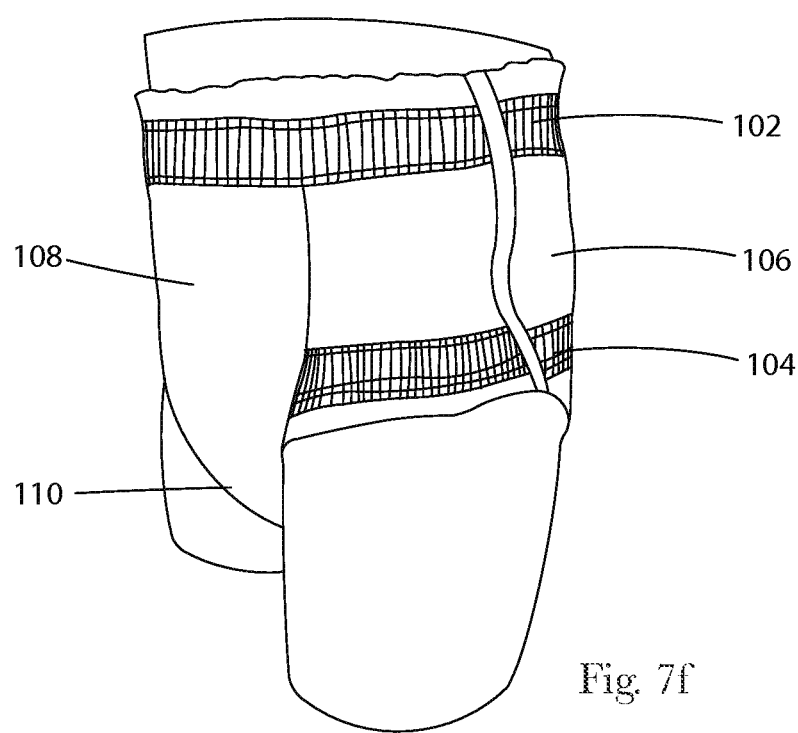
FIG. 7*f* is a perspective view of an exemplary disposable pull-on garment in a typical in-use configuration.

In the embodiment shown in FIG. 6b, the absorbent article 20 may comprise a first graphic zone 102 disposed at or adjacent the waist edge 134, 138, and a main body graphic zone 108 disposed on the center of the first waist region 26 and/or the second waist region 28, such that one or both of the first graphic zone 102 and the main body graphic zone 108 are disposed at the side seams 32 of the absorbent article 20. The first graphic zone 102 is disposed at or adjacent the waist opening 36 and extends circumferentially about the first 26 and/or second waist region 28. As shown in the embodiment of FIG. 6b, the first graphic zone 102 may comprise an indicia 46. The indicia 46 may also be present in the main body graphic zone 108. Thus, the first graphic zone 102 and the main body graphic zone 108 may be coordinated to create a composite graphical element that may or may not be uniform. The indicia 46 may be formed through printing, aperturing and/or texturing of the material in the particular graphic zone(s).

As further shown in FIG. 6b, a crotch region graphic zone 110 may be disposed at or adjacent a leg opening 34 and extend circumferentially about at least a portion of the leg opening 34, wherein the first graphic zone 102 and the crotch region graphic zone 110 are coordinated to create a composite graphical element that may or may not be uniform. Thus, in this embodiment, the first graphic zone 102 is disposed at the side seam 32, a waist edge 134, 138, and at least a portion of the leg opening 34. In alternate embodiments, the entirety of the side seam 32 and the entirety of the waist edge 134, 138 are disposed in the first graphic zone 102.

FIGS. 7a-7f are additional perspective views of exemplary disposable pull-on garments in a typical in-use configuration.

The dimensions and values disclosed herein are not to be understood as being strictly limited to the exact numeral values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising at least one elastomeric belt, a first waist region, a second waist region, and a crotch region, wherein the first waist region and second waist region are joined with each other such that a pair of side seams are formed such that the absorbent article comprises two leg openings and a waist opening, wherein at least one of the first waist region and the second waist region comprise: at least a portion of a main body graphic zone, a first graphic zone, a second graphic zone, and a third graphic zone, wherein the first graphic zone, the second graphic zone, and the third graphic zone are disposed at a side seam of the absorbent article, and wherein the first graphic zone, the second graphic zone, and the third graphic zone are all disposed on the at least one elastomeric belt, and wherein the main body graphic zone is disposed on a main body of the absorbent article underneath the at least one elastomeric belt, and wherein the crotch region comprises a crotch region graphic zone such that the second graphic zone and the crotch region graphic zone are aligned to create a uniform graphical element, and the crotch region graphic zone is not underlying the at least one elastomeric belt.

2. The absorbent article of claim 1, wherein the first graphic zone is disposed at a waist edge and extends circumferentially about the first waist region and the second waist region of the absorbent article.

3. The absorbent article of claim 1, wherein the third graphic zone is disposed between the first graphic zone and the second graphic zone and extends circumferentially about at least portions of the first waist region and the second waist region of the absorbent article.

4. The absorbent article of claim 1, wherein a longitudinal axis of the absorbent article extends through the first graphic zone and the third graphic zone but not the second graphic zone.

5. The absorbent article of claim 1, wherein the main body graphic zone is disposed on the main body of the absorbent article underneath a portion of the third graphic zone.

6. The absorbent article of claim 1, wherein the transition between the second graphic zone and the crotch region graphic zone extends from the side seam to the leg opening forming a uniform graphical element around the leg opening.

7. An absorbent article comprising at least one elastomeric belt, a first waist region, a second waist region, and a crotch region, wherein the first waist region and second waist region are joined with each other such that a pair of side seams are formed such that the absorbent article comprises two leg openings and a waist opening, wherein at least one of the first waist region and the second waist region comprise: a first graphic zone disposed adjacent the waist edge, a second graphic zone is disposed at a leg opening and extends circumferentially about at least a portion of the leg opening, and a main body graphic zone disposed on the center of the first waist region or the second waist region, wherein the first graphic zone and the main body graphic zone are disposed at the side seams of the absorbent article, wherein the main body graphic zone is disposed on a main body of the absorbent article underneath the at least one elastomeric belt, and wherein the crotch region comprises a crotch region graphic zone such that the second graphic zone and the crotch region graphic zone are aligned to create a uniform graphical element, and the crotch region graphic zone is not underlying the at least one elastomeric belt.

8. The absorbent article of claim 7, wherein the first waist region is a first elastomeric belt, and the second waist region is a second elastomeric belt, and the first graphic zone is disposed on at least one of the first or second elastomeric belt.

9. The absorbent article of claim 7, wherein the first graphic zone is disposed adjacent the waist opening and extends circumferentially about the first and second waist region.

10. The absorbent article of claim 7, wherein the first graphic zone comprises an indicia, wherein the indicia of the first graphic zone comprises indication of the front and/or back side of the article.

11. The absorbent article of claim 7, wherein the first graphic zone and the main body graphic zone are coordinated to create a uniform graphical element.

12. The absorbent article of claim 7, further comprising a crotch region graphic zone disposed at a leg opening and extending circumferentially about at least a portion of the leg opening, wherein the first graphic zone and the crotch region graphic zone are coordinated to create a uniform graphical element.

13. The absorbent article of claim 7, wherein the first graphic zone is disposed at the side seam, a waist edge, and at least a portion of the leg opening.

14. The absorbent article of claim 7, wherein the entirety of the side seam and the entirety of the waist edge are disposed in the first graphic zone.

\* \* \* \* \*